United States Patent [19]

Wright, Jr. et al.

[11] Patent Number: 4,489,089
[45] Date of Patent: Dec. 18, 1984

[54] SUBSTITUTED N-[ω-(1H-IMIDAZOL-1-YL)ALKYL]-AMIDES

[75] Inventors: William B. Wright, Jr., Woodcliff Lake, N.J.; Jeffrey B. Press, Tuxedo, N.Y.

[73] Assignee: American Cyanamid Company, Stamford, Conn.

[21] Appl. No.: 570,159

[22] Filed: Jan. 13, 1984

Related U.S. Application Data

[63] Continuation-in-part of Ser. No. 482,388, Apr. 6, 1983, abandoned.

[51] Int. Cl.³ .................... A01N 43/50; C07D 233/64
[52] U.S. Cl. ................................. 424/273 R; 548/336
[58] Field of Search .................... 548/336; 424/273 R

[56] References Cited

U.S. PATENT DOCUMENTS 3,646,057  2/1972  Beaman et al. .................... 548/338

Primary Examiner—Alan L. Rotman
Assistant Examiner—Kurt G. Briscoe
Attorney, Agent, or Firm—Edward A. Conroy, Jr.

[57] ABSTRACT

This disclosure describes novel N-[ω-(1H-imidazol-1-yl)alkyl]amides which possess the property of inhibiting the enzyme thromboxane synthetase.

13 Claims, No Drawings

SUBSTITUTED N-[ω-(1H-IMIDAZOL-1-YL)ALKYL]-AMIDES

CROSS REFERENCE TO RELATED APPLICATION

This application is a continuation-in-part of our co-pending application Ser. No. 482,388, filed Apr. 6, 1983, now abandoned.

BRIEF SUMMARY OF THE INVENTION

This invention relates to new organic compounds and, more particularly, is concerned with novel substituted N-[ω-(1H-imidazol-1-yl)alkyl]amides which may be represented by the following structural formula:

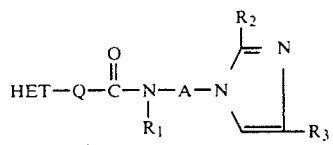

wherein A is a divalent moiety of the formulae:

$-C_nH_{2n}-$ or $-CH_2CH=CHCH_2-$ wherein n is an integer from 2 to 8, inclusive; $R_1$ is hydrogen, alkyl having from one to three carbon atoms or benzyl; $R_2$ and $R_3$ may be the same or different and are each hydrogen, alkyl having from one to three carbon atoms or phenyl; Q is a divalent moiety of the formulae:

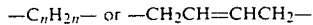

wherein m is zero, 1, 2 or 3; and HET is a heterocyclic moiety of the formulae:

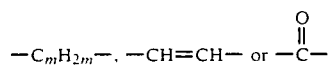

wherein Y is oxo (—O—) or thio (—S—); $R_4$ is hydrogen, halogen, dihalogen, lower alkyl or nitro; and $R_5$ is hydrogen or halogen. Suitable lower alkyl groups are those having up to three carbon atoms whereas halogen is exemplified by fluoro, chloro and bromo.

The organic bases of this invention form non-toxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, sulfamic, maleic, lactic, malic, succinic, tartaric, acetic, fumaric, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

DETAILED DESCRIPTION OF THE INVENTION

The novel compounds of the present invention may be readily prepared as set forth in the following reaction schemes wherein A, $R_1$, $R_2$, $R_3$, Q and HET are as hereinbefore defined; $R_6$ is alkyl having from one to three carbon atoms or benzyl; and X is chloro, bromo or a moiety of the formula:

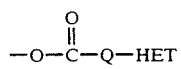

wherein Q and HET are as hereinabove defined and the resulting anhydride is symmetrical.

METHOD I

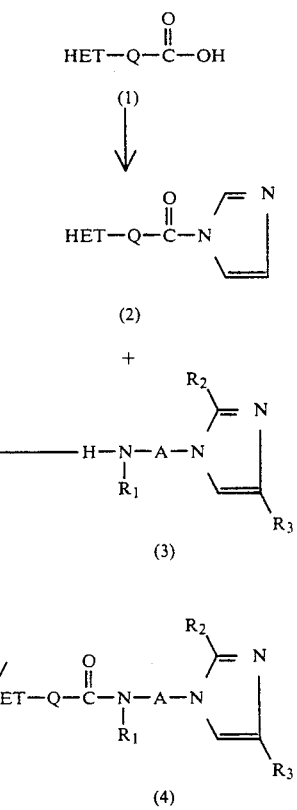

In accordance with Method I, an appropriately substituted acid (1) is reacted with 1,1'-carbonyldiimidazole in an inert solvent such as dioxane, dimethylformamide or tetrahydrofuran at ambient temperatures for 1-3 hours to provide the intermediates (2). Treatment of the intermediates (2) with an appropriately substituted 1H-imidazole-1-alkanamine (3), either as the free base or a salt thereof, provides the final products (4). The final condensation of (2)+(3) is best carried out by merely adding (3) to the reaction mixture containing (2) and then heating at the reflux temperature for 1-5 hours. Concentration of the reaction mixture followed by the addition of aqueous base (KOH or NaOH) in a solvent such as $CHCl_3$ or $CCl_4$ and isolation from the organic phase provides the products (4) as the free bases.

METHOD II

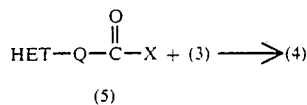

In accordance with Method II, an appropriately substituted acid halide or acid anhydride (5) is condensed with an appropriately substituted 1H-imidazole-1-alkanamine (3), either as the free base or a salt thereof, to provide the final products (4). This condensation is best carried out at ambient temperatures for up to 18 hours in an inert solvent such as $CH_2Cl_2$, $CHCl_3$ or $CCl_4$ and in the presence of an acid acceptor such as aqueous base (2N KOH or 2N NaOH), soda ash or concentrated (12%) aqueous ammonia. The resulting organic phase is then washed with water, dried, and concentrated to give the crystalline products (4) as the free bases.

METHOD III

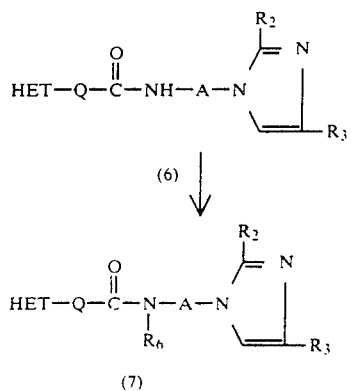

In accordance with Method III, an appropriately substituted N-[w-(1H-imidazol-1-yl)alkyl]amide (6) is treated with sodium hydride in an inert solvent such as dioxane, dimethylformamide or tetrahydrofuran at ambient temperature for 1-3 hours to form the intermediate sodium salt in situ. Addition to the reaction mixture of an alkyl halide of the formula: $R_6$—Hal (wherein Hal is chloro, bromo or iodo), followed by stirring at ambient temperatures for 12-24 hours provides the alkylated derivative (7). Isolation of (7) is readily accomplished by concentration of the reaction mixture, dilution with water, and extraction into a water insoluble solvent such as $CH_2Cl_2$, $CHCl_3$ or $CCl_4$.

The compounds of this invention inhibit thromboxane synthetase enzyme. Thus, these compounds are useful in the treatment of diseases characterized by an imbalance of thromboxane $A_2$/prostacyclin such as ischemic heart disease, transient ischemic attack, thrombosis and migraine. Recent reviews have established the role of the thromboxane/prostacyclin balance in the vascular system [(Cardiovascular Diseases: New Trends in Surgical and Medical Aspects, H. Barnett, P. Paoletti, E. Flamm and G. Brambilla, eds., Elsevier/North-Holland Biomedical Press, pp 137-150 (1981)]. Prostacyclin ($PGI_2$) is a potent vasodilator and platelet aggregation inhibitor, whereas thromboxane ($TXA_2$) is a powerful vasoconstrictor and causative of platelet aggregation. $TXA_2$ is synthesized by thromboxane synthetase enzyme located in, for example, blood platelets. When $TXA_2$ production is increased relative to $PGI_2$, platelet aggregation, thrombosis and vasospasm may occur [Lancet (i), 1216 (1977); Lancet, 479 (1977); Science, 1135 (1976); Amer. J. Cardiology, 41, 787 (1978)]. $TXA_2$ synthetase inhibitors have been shown to have superior anti-thrombotic action to that of aspirin [J. Clin. Invest., 65, 400 (1980); Br. J. Pharmac., 76, 3 (1982)].

The role of prostaglandins including $TXA_2$ and $PGI_2$ in ischemic heart patients has been reviewed [Cardiovascular Pharmacology of the Prostaglandins, A. G. Herman, P. M. Vanhoute, H. Denolin and A. Goosens, eds., Raven Press, New York, pp 361-374 (1982)]. Injection of $TXA_2$ into coronary arteries of guinea pigs and rabbits causes myocardial ischemia and subendocardial necrosis [Drugs of the Future, 7, 331 (1982); Proc. Jap. Acad., 53(B), 38 (1977); Eur. J. Pharmacol., 53 49(1978)]. Recent research has demonstrated the beneficial effects of $PGI_2$ and selective inhibition of thromboxane synthetase on ischemic myocardium in canines [J. Cardiovascular Pharmacology, 4, 129 (1982)]. Thus compounds which selectively inhibit thromboxane synthetase (and hence $TXA_2$) without adversely affecting $PGI_2$ are useful in the treatment of vascular diseases such as ischemia and migraine. In addition, inhibition of $TXA_2$ formation may effectively treat platelet aggregation and prevent thrombosis.

Under urethan anesthesia, 10 $\mu$l. of arterial blood was collected in one ml. of 3.2% sodium citrate in a polystyrene tube from Okamoto-Aoki spontaneously hypertensive rats (SHR) (Taconic Farms, Germantown, NY) between 19 and 24 weeks in age. The blood was diluted with 3 ml. cold saline and centrifuged at room temperature for 15 minutes at 460×g. The platelet rich plasma (PRP) was separated. The platelets were isolated by centrifuging the PRP for 10 minutes at 1060×g and were washed in 4 ml. cold oxygenated Krebs phosphate buffer, pH 7.4. The chilled platelets recovered from centrifuging at 800×g for 10 minutes were resuspended in oxygenated Krebs phosphate buffer and diluted to contain $4.5-6.0 \times 10^4$ platelets/$\mu$l.

The inhibition of thromboxane (TX) formation was studied by determing the concentration of thromboxane $B_2$ ($TXB_2$), the stable hydrolysis product of $TXA_2$. Assay samples, prepared on ice, contained 200 $\mu$l. platelet suspension, 50 $\mu$l. saline, and 50 $\mu$l. vehicle or drug under study (OKY-1581, UK-37248-01, 1-benzylimidazole, or indomethacin). The samples were incubated for 10 minutes at 37° C. in a metabolic shaker. The reaction was terminated by immersing the tubes in an ice bath and adding 50 $\mu$l. of 0.5M citric acid. The samples were centrifuged for 10 minutes in a refrigerated centrifuge and the supernatants thus obtained were decanted and stored at $-20°$ C. The $TXB_2$ content for each sample was determined by a direct radioimmunoassay (RIA) utilizing a $TXB_2$ specific RIA kit purchased from New England Nuclear, Boston, MA and expressed as pg $TXB_2$ formed minute$^{-1}$ sample$^{-1}$, from which the percent inhibition of $TXB_2$ formation was calculated. The results of this test on representative compounds of this invention appear in Table I

TABLE I

| Compound | Dose | % Inhibition |
|---|---|---|
| N—[3-(1H—imidazol-1-yl)propyl]-2-furanecarboxamide | $10^{-4}$M | 97 |
| 3-chloro-N—[3-(1H—imidazol-1-yl)propyl]benzo[b]thiophene-2-carboxamide | $10^{-4}$M | 100 |

TABLE I-continued

| Compound | Dose | % Inhibition |
|---|---|---|
| 3-chloro-6-fluoro-N—[3-(1H—imidazol-1-yl)propyl]benzo[b]thiophene-2-carboxamide | $10^{-4}$M | 96 |
| 3-chloro-N—[3-(1H—imidazol-1-yl)propyl]-6-methyl-benzo[b]thiophene-2-carboxamide | $10^{-4}$M | 96 |
| N—[3-(1H—imidazol-1-yl)propyl]-3-furanecarboxamide | $10^{-4}$M | 78 |
| 5-bromo-N—[3-(1H—imidazol-1-yl)propyl]-2-furanecarboxamide | $10^{-4}$M | 82 |
| N—[3-(1H—imidazol-1-yl)propyl]-2-thiophenecarboxamide | $10^{-4}$M | 93 |
| N—[3-(1H—imidazol-1-yl)propyl]-5-methyl-2-thiophenecarboxamide | $10^{-4}$M | 96 |
| 4,5-dibromo-N—[3-(1H—imidazol-1-yl)propyl]-2-thiophenecarboxamide | $10^{-4}$M | 100 |
| N—[3-(1H—imidazol-1-yl)propyl]-2-benzofuranecarboxamide | $10^{-4}$M | 97 |
| 5-chloro-N—[3-(1H—imidazol-1-yl)propyl]benzo[b]thiophene-2-carboxamide | $10^{-4}$M | 100 |
| N—[3-(1H—imidazol-1-yl)propyl]-3-(2-furanyl)-2-propenamide | $10^{-4}$M | 78 |
| N—[3-(1H—imidazol-1-yl)propyl]-3-(2-thienyl)-2-propenamide | $10^{-4}$M | 100 |
| N—[3-(1H—imidazol-1-yl)propyl]-5-nitro-2-furanecarboxamide | $10^{-4}$M | 64 |
| N—[3-(1H—imidazol-1-yl)propyl]-α-oxo-thiophene acetamide | $10^{-4}$M | 73 |
| 3-chloro-N—[2-(1H—imidazol-1-yl)ethyl]benzo[b]thiophene-2-carboxamide | $10^{-4}$M | 70 |
| 3-chloro-N—[3-(2-ethyl-1H—imidazol-1-yl)propyl]benzo[b]thiophene-2-carboxamide | $10^{-4}$M | 55 |
| 3-chloro-N—[3-(4-methyl-1H—imidazol-1-yl)propyl]benzo[b]thiophene-2-carboxamide | $10^{-4}$M | 98 |
| N—[4-(1H—imidazol-1-yl)butyl]-2-furanecarboxamide | $10^{-4}$M | 87 |
| 3-chloro-N—[4-(1H—imidazol-1-yl)butyl]benzo[b]thiophene-2-carboxamide | $10^{-4}$M | 91 |
| N—[4-(1H—imidazol-1-yl)butyl]thiophene-2-carboxamide | $10^{-4}$M | 95 |
| 5-chloro-N—[3-(1H—imidazole-1-yl)propyl]thiophene-2-carboxamide | $10^{-4}$M | 95 |
| N—[3-(4-methyl-1H—imidazol-1-yl)propyl]thiophene-2-carboxamide | $10^{-4}$M | 51 |

The novel compounds of the present invention are also active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, N.Y. having an average mean arterial blood pressure of 160±1.5 mm of mercury are used in the test. One to 3 rats are used per test compound. A rat is dosed by gavage with a test compound, suspended in 2% pre-boiled starch at a concentration of 50 mg/ml, at a dose of 100 mg/kg of body weight or less, with 0.9% sodium chloride loading at a dose 25 ml/kg of body weight. A second identical dose of the test compound, without sodium chloride loading is given 24 hours later. At 28 hours after the initial dose, the mean arterial blood pressure (MABP) is measured by the method of Chan and Poorvin vide supra. The procedure is repeated in a second and third rat when necessary. Based on the data obtained and using the three-stage "sequential probability ratio test" statistical method, the critieria for activity or retest are as follows:

If the blood pressure in the first rat is ≦116 mm mercury the compound is considered active. If the blood pressure is between 117 and 146 mm, a second rat is used. If the average blood pressure of the first and second rats is ≦122 mm the compound is considered active. If the average blood pressure is between 123 and 137 mm, a third rat is used. If the average blood pressure of the three rats is ≦128 mm the compound is considered active. The results of this test on representative compounds of the present invention appear in Table II below.

TABLE II

| Compound | MABP/mm Hg (no. of rats) |
|---|---|
| N—[3-(1H—imidazol-1-yl)propyl]-3-furanecarboxamide | 128 (3) |
| N—[3-(1H—imidazol-1-yl)propyl-5-nitro-2-furanecarboxamide | 114 (3) |
| N—[3-(1H—imidazol-1-yl)propyl]-6O-oxo-thiophene acetamide | 125 (3) |
| 3-chloro-N—[2-(1H—imidazol-1-yl)ethyl]-benzo[b]thiophene-2-carboxamide | 117 (3) |
| N—[4-(1H—imidazol-1-yl)butyl]thiophene-2-carboxamide | 114 (2) |
| 5-chloro-N—[3-(1H—imidazol-1-yl)propyl]-thiophene-2-carboxamide | 125 (3) |
| 5-chloro-N—[4-(1H—imidazol-1-yl)butyl]-thiophene-2-carboxamide | 118 (2) |
| N—[3-(1H—imidazol-1-yl)propyl]thiophene-2-butanamide | 121 (2) |

The novel compounds of the present invention have been found to be highly useful for inhibiting thromboxane synthetase in mammals when administered in amounts ranging from about 0.1 mg. to about 20.0 mg/kg of body weight per day. A preferred dosage regimen for optimum results would be from about 0.5 mg. to about 10.0 mg/kg of body weight per day. Such dosage units are employed that a total of from about 35 to about 700 mg. of active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weight of from about 200 to 1500. Although the amount of active compound dissolved in the above vehicle may vary from 0.10% to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentration of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, intital concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, waters, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propyl parabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

N-[3-(1H-Imidazol-1-yl)propyl]-2-furanecarboxamide

Following the procedure of Schwan, J. Het. Chem. 4, 633 (1967), 25 ml. of acrylonitrile was heated to 70° C. A 13.6 g. portion of imidazole was added and the mixture was gradually heated to 90°-100° C. and maintained at that temperature for 3 hours. The mixture was then concentrated in vacuo to remove excess acrylonitrile, taken up in methanol and reconcentrated. The concentrate was added to 150 ml. of methanol, 100 ml. of concentrated ammonium hydroxide and 8 g. of Raney nickel catalyst in a Parr apparatus and subjected to hydrogenation at an initial pressure of 53 psi. After approximately 6 hours and the uptake of 32 psi. of hydrogen, the mixture was filtered. The filtrate was concentrated to remove the solvent, then concentrated once from ethanol, giving 1H-imidazole-1-propanamine as an oil. When this was added to 250 ml. of methanolic hydrogen chloride, concentrated to remove the solvent, boiled with 100 ml. of ethanol and then refrigerated, 20.3 g. of 1H-imidazole-1-propanamine dihydrochloride was obtained as a tan solid, m.p. 146°-150° C.

A mixture of 1.98 g. of 1H-imidazole-1-propanamine dihydrochloride and 30 ml. of 1N sodium hydroxide was stirred at room temperature. A mixture of 0.98 ml. of 2-furanyl chloride and 50 ml. of dichloromethane was added and stirring was continued overnight. More dichloromethane was added, the organic layer was separated, washed twice with water and concentrated, giving 1.0 g. of the desired product, m.p. 111°-113° C.

Following the procedure of this example but using 1H-imidazole-1-propanamine dihydrochloride and the indicated acid chlorides, the products of Examples 2-4, listed in Table III, were obtained.

TABLE III

| Ex. | Acid Chloride | Product | m.p. °C. |
|---|---|---|---|
| 2 | 3-chloro-benzo[b]thiophene-2-carbonyl chloride | 3-chloro-N—[3-(1H—imidazol-1-yl)propyl]benzo[b]thiophene-2-carboxamide | 133-135 |
| 3 | 3-chloro-6-fluoro-benzo[b]thiophene-2-carbonyl chloride | 3-chloro-6-fluoro-N—[3-(1H—imidazol-1-yl)propyl]benzo[b]thiophene-2-carboxamide | 127-129 |
| 4 | 3-chloro-6-methyl-benzo[b]thiophene-2-carbonyl chloride | 3-chloro-N—[3-(1H—imidazol-1-yl)propyl]-6-methyl-benzo[b]thiophene-2-carboxamide | 122-125 |

EXAMPLE 5

N-[3-(1H-Imidazol-1-yl)propyl]-3-furanecarboxamide

A solution of 2.24 g. of furoic acid, 3.24 g. of N,N'-carbonyldiimidazole and 80 ml. of tetrahydrofuran was allowed to stir at room temperature for 2 hours. A 4.0 g. portion of 1H-imidazole-1-propanamine dihydrochloride was added and the mixture was stirred at room temperature overnight. The mixture was then heated for 5 hours, 5 ml. of water was added, heating resumed for 30 minutes and then the mixture was concentrated to remove most of the solvent. Dichloromethane and 60 ml. of 1N sodium hydroxide were added, the organic layer was separated, washed twice with water, dried and concentrated, giving 2.0 g. of the desired product, m.p. 127°-129° C.

The fumarate salt of this and the other products of this invention may be prepared by warming a mixture of one mole of the product (e.g., N-[3-(1H-imidazol-1-yl)propyl]-2-thiopheneacetamide), one mole of fumaric acid and ethanol to solution and then diluting with ether. The resulting crystals are collected, washed with ether and dried.

Following the procedure of this example but using 1H-imidazole-1-propanamine dihydrochloride and the indicated acids (and optionally converting to the fumarate salt), the products of Examples 6–19, listed in Table IV, were obtained.

TABLE IV

| Ex. | Acid | Product | m.p. °C. |
|---|---|---|---|
| 6 | 5-bromo-2-furoic acid | 5-bromo-N—[3-(1H—imidazol-1-yl)propyl]-2-furanecarboxamide | 139–142 |
| 7 | 2-thiophene carboxylic acid | N—[3-(1H—imidazol-1-yl)propyl]-2-thiophenecarboxamide | 135–137 |
| 8 | 5-methyl-2-thiophene carboxylic acid | N—[3-(1H—imidazol-1-yl)propyl]-5-methyl-2-thiophenecarboxamide | 120–122 |
| 9 | 4,5-dibromo-2-thiophene carboxylic acid | 4,5-dibromo-N—[3-(1H—imidazol-1-yl) propyl]-2-thiophenecarboxamide | 126–128 |
| 10 | coumarilic acid | N—[3-(1H—imidazol-1-yl)propyl]-2-benzofuranecarboxamide | 105–107 |
| 11 | 5-chloro-benzo[b]thiophene-2-carboxylic acid | 5-chloro-N—[3-(1H—imidazol-1-yl)propyl]benzo[b]thiophene-2-carboxamide | 155–157 |
| 12 | 2-thiophene acetic acid | N—[3-(1H—imidazol-1-yl)propyl]-2-thiophene tamide, fumarate | 85–87 |
| 13 | 3-thiophene acetic acid | N—[3-(1H—imidazol-1-yl)proyl]-3-thiopheneacetamide, fumarate | 84–86 |
| 14 | 3-(2-furoyl) acrylic acid | N—[3-(1H—imidazol-1-yl)propyl]-3-(2-furanyl)-2-propenamide | 77–80 |
| 15 | 3-(2-thienyl) acrylic acid | N—[3-(1H—imidazol-1-yl)propyl]-3-(2-thienyl)-2-propenamide | 70–80 |
| 16 | 5-nitro-2-furoic acid | N—[3-(1H—imidazol-1-yl)propyl-5-nitro-2-furanecarboxamide | 151–153 |
| 17 | 4-(2-thienyl) butyric acid | N—[3-(1H—imidazol-1-yl)propyl]-2-thiophenebutyramide | oil |
| 18 | 2-thiophene glyoxylic acid | N—[3-(1H—imidazol-1-yl)propyl]-α-oxo-thiophene acetamide | 88–90 |
| 19 | 5-chloro-2-thiophene carboxylic acid | 5-chloro-N—[3-(1H—imidazol-1-yl)propyl]thiophene-2-carboxamide | 144–147 |

EXAMPLE 20

3-Chloro-N-[2-(1H-imidazol-1-yl)ethyl]benzo[b]thiophene-2-carboxamide

A mixture of 18.0 g. of sodium imidazole, 50.8 g. of N-(2-bromoethyl)phthalimide and 300 ml. of toluene was refluxed for 24 hours. Most of the toluene was decanted and concentrated to remove the solvents. The residue was refrigerated overnight, then filtered and washed with diethyl ether. The solid was dissolved in 14 ml. of isopropanol and cooled, giving 9.2 g. of 2-[2-(1H-imidazol-1-yl)ethyl]-isoindole-1,3(2H)-dione.

A mixture of 8.0 g. of 2-[2-(1H-imidazol-1-yl)-ethyl]-isoindole-1,3(2H)-dione, 1.75 ml. of hydrazine hydrate and 120 ml. of ethanol was stirred and refluxed and 3 hours, then cooled and 165 ml. of 10% hydrochloric acid was added. Refluxing was continued for one hour, then the mixture was concentrated to dryness, stirred with 135 ml. of 10% hydrochloric acid and filtered. The aqueous layer was concentrated to dryness, boiled with 170 ml. of ethanol and the white solid collected, giving 4.3 g. of 1H-imidazole-1-ethanamine dihydrochloride.

A 1.47 g. portion of 1H-imidazole-1-ethanamine dihydrochloride was reacted with 3-chloro-benzo[b]thiophene-2-carbonyl chloride as described in Example 1, giving 0.75 g. of the desired product, m.p. 132°–134° C.

In like manner, the reaction of 1H-imidazole-1-ethaneamine dihydrochloride with 2-furoyl chloride by the procedure of Example 1 provided N-[2-(1H-imidazol-1-yl)ethyl]-2-furanecarboxamide, m.p. 131°–133° C.

Following the procedure of this example, N-(3-bromopropyl)phthalimide with 4-methylimidazole and 2-ethylimidazole were used to produce respectively 2-[3-(4-methyl-1H-imidazol-1-yl)propyl]isoindole-1,3-(2H)-dione and 2-[3-(2-ethyl-1H-imidazol-1-yl)-propyl]isoindole-1,3(2H)-dione which again following the procedure of this example were converted respectively to (4-methyl-1H-imidazol-1-yl)-1-propanamine dihydrochloride and (2-ethyl-1H-imidazol-1-yl)-1-propanamine dihydrochloride which were then converted by the procedure of Example 1, using the appropriate acid chloride, to the products of Examples 21–27, listed in Table V.

TABLE V

| Ex. | Acid Chloride | Product | m.p. °C. |
|---|---|---|---|
| 21 | 2-furanyl chloride | N—[3-(2-ethyl-1H—imidazol-1-yl)propyl]-2-furanecarboxamide | 81–83 |
| 22 | 3-chloro-benzo[b]-thiophene-2-carbonyl chloride | 3-chloro-N—[3-(2-ethyl-1H—imidazol-1-yl-propyl]-benzo[b]thiophene-2-carboxamide | 120–122 |
| 23 | 2-furanyl chloride | N—[3-(4-methyl-1H—imidazol-1-yl)propyl]-2-furanecarboxamide | oil |
| 24 | 3-chloro-benzo[b]-thiophene-2-carbonyl chloride | 3-chloro-N—[3-(4-methyl-1H—imidazol-1-yl)propyl]benzo[b]thiophene-2-carboxamide | 120–135 |
| 25 | 2-thenoyl chloride | N—[3-(4-methyl-1H—imidazol-1-yl)propyl]thiophene-2-carboxamide | |
| 26 | 4-chloro-2-thenoyl chloride | 4-chloro-N—[3-(4-methyl-1H—imidazol-1-yl)propyl]-thiophene-2-carboxamide | |
| 27 | 4-chloro-2-thenoyl chloride | 4-chloro-N—[3-(2-ethyl-1H—imidazol-1-yl)propyl]-thiophene-2-carboxamide | |

EXAMPLE 28

N-[4-(1H-Imidazol-1-yl)butyl]-2-furanecarboxamide

A mixture of 6.3 g. of sodium imidazole, 100 ml. of dimethylformamide and 19.7 g. of N-(4-bromobutyl)-phthalimide was heated on a steam bath for 6 hours and then concentrated to remove volatile material. The residue was boiled with 150 ml. of toluene and the toluene layer was decanted and concentrated. The residue was triturated with diethyl ether and cooled, giving N-[4-(1H-imidazol-1-yl)butyl]-isoindole-1,3(2H)-dione (m.p. 75°–77° C.) which was recovered by filtration.

A mixture of 10.0 g. of N-[4-(1H-imidazol-1-yl)-butyl]isoindole-1,3(2H)-dione, 1.97 ml. of hydrazine hydrate and 100 ml. of ethanol was heated at reflux for 3 hours and then cooled. A 160 ml. of portion of 3N hydrochloric acid was added, the mixture was heated at reflux for one hour and then concentrated. The residue was stirred with 150 ml. of 3N hydrochloric acid and then filtered. The mother liquor was concentrated to dryness, diluted with 10 ml. of ethanol and cooled, giving 1H-imidazole-1-butanamine dihydrochloride (m.p. 132°–146° C.) which was recovered by filtration.

When the above procedure is carried out substituting the appropriate N-(bromoalkyl)phthalimide for N-(4-bromo-butyl)phthalimide; 1H-imidazole-1-pentanamine, gamma-methyl-1H-imidazole-1-propanamine, 1H-imidazole-1-hexanamine, 1H-imidazole-1-heptanamine and 1H-imidazole-1-octylamine as their dihydrochloride salts are obtained.

A portion of 1H-imidazole-1-butanamine dihydrochloride was then reacted with furoyl chloride as described in Example 1, giving the desired product, m.p. 88°–90° C.

Using the same procedure, the appropriate acid chlorides were converted to the products of Examples 29–31 listed in Table VI below.

TABLE VI

| Ex. | Acid Chloride | Product | m.p. °C. |
|---|---|---|---|
| 29 | 3-chloro-benzo[b]-thiophene-2-carbonyl chloride | 3-chloro-N—[4-(1H—imidazol-1-yl)-butyl]benzo[b]thiophene-2-carboxamide | 84–86 |
| 30 | 5-chloro-thiophene-2-carbonyl chloride | 5-chloro-N—[4-(1H—imidazol-1-yl)-butyl]thiophene-2-carboxamide | 144–147 |
| 31 | 2-thenoyl chloride | N—[4-(1H—imidazol-1-yl)butyl]thiophene-2-carboxamide | 103–106 |

EXAMPLE 32

N-[3-(4-phenyl-1H-imidazol-1-yl)propyl]-2-furanecarboxamide

A mixture of 28.8 g. of 4-phenylimidazole and 25 ml. of acrylonitrile was heated at reflux temperature for 6 hours and then concentrated to remove the volatile material. The residue was mixed with 200 ml. of ethanol, 100 ml. of ammonium hydroxide and 6 g. of Raney Nickel catalyst and reduced in a Parr hydrogenator under hydrogen pressure until reduction was complete. The catalyst was removed by filtration and the filtrate was concentrated to remove the solvents. The residual oil was 4-phenyl-1H-imidazole-1-propanamine.

A mixture of 2.0 g. of 4-phenyl-1H-imidazole-1-propanamine, 50 ml. of methylenechloride and 10 ml. of 1N sodium hydroxide was stirred and 2.0 ml. of 2-furoyl chloride was added. The mixture was stirred for eighteen hours, methylene chloride was added and the layers were separated. The organic layer was washed with water, dried over magnesium sulfate and concentrated. The residue was washed onto a filter with diethyl ether, giving the desired product, m.p. 120°–122° C.

EXAMPLE 33

N-[3-(2-phenyl-1H-imidazol-1-yl)propyl]-2-furanecarboxamide

A mixture of 28.8 g. of 2-phenylimidazole and 25 ml. of acrylonitrile was heated at reflux temperature for 6 hours and then concentrated to remove the volatile material. The residue was mixed with 200 ml. of ethanol, 100 ml. of ammonium hydroxide and 6 g. of Raney Nickel catalyst and reduced in a Parr hydrogenator under hydrogen pressure until reduction was complete. The catalyst was removed by filtration and the filtrate was concentrated to remove the solvents. The residual oil was 2-phenyl-1H-imidazole-1-propanamine.

A mixture of 2.0 g. of 2-phenyl-1H-imidazole-1-propanamine, 50 ml. of methylenechloride and 10 ml. of 1N sodium hydroxide was stirred and 2.0 ml. of 2-furoyl chloride was added. The mixture was stirred for eighteen hours, methylene chloride was added and the layers were separated. The organic layer was washed with water, dried over magnesium sulfate and concentrated. The desired product was obtained as an oil.

EXAMPLE 34

N-Benzyl-N-[3-(1H-imidazol-1-yl)propyl]-2-thiophene carboxamide

A mixture of 4.7 g. of N-[3-(1H-imidazol-1-yl)propyl]-2-thiophene carboxamide, 40 ml. of dimethylformamide, and 0.96 g. of 50% sodium hydride in oil was stirred for 2 hours and 2.62 g. of benzyl bromide was added. The mixture was stirred for 24 hours, concentrated to remove the dimethyl formamide, diluted with water and methylene chloride, and the layers separated. The organic layer was washed with water, dried over magnesium sulfate, and concentrated. The oil was twice washed with hexane and again concentrated. The desired product was obtained as an oil.

EXAMPLE 35

N-Ethyl-N-[3-(1H-imidazol-1-yl)propyl]-2-thiophene carboxamide

The above compound is obtained when ethyl bromide is substituted for benzyl bromide in the procedure of Example 34.

EXAMPLE 36

5-Chloro-N-[5-(1H-imidazol-1-yl)pentyl]-2-thiophene carboxamide

A solution of 1.8 g. of 5-chlorothiophene-2-carbonyl chloride in 10 ml. of $CH_2Cl_2$ was added to a mixture of 1.52 g. of 1H-imidazole-1-pentanamine, 10 ml. of 1N NaOH and 50 ml. of $CH_2Cl_2$. The reaction mixture was stirred for 20 hours and then treated with 25 ml. of $CH_2Cl_2$ and 5 ml. of 1N NaOH. The layers were separated and the organic layer was washed with water, dried over $MgSO_4$ and concentrated. The crystalline residue was washed with diethyl ether whereby the desired product, m.p. 123°–125° C., was obtained.

EXAMPLE 37

5-Chloro-N-[6-(1H-imidazol-1-yl)hexyl]-2-thiophene carboxamide

The title compound, m.p. 96°–98° C., was obtained when 5-chlorothiophene-2-carbonyl chloride was reacted with 1H-imidazole-1-hexanamine by the procedure of Example 36.

EXAMPLE 38

5-Chloro-N-[8-(1H-imidazol-1-yl)octyl]-2-thiophene carboxamide

When 1H-imidazole-1-octylamine is treated with 5-chlorothiophene-2-carbonyl chloride by the procedure of Example 36, the title compound, m.p. 95°–97° C., was obtained.

EXAMPLE 39

5-Chloro-N-[3-(1H-imidazol-1-yl)butyl]-2-thiophene carboxamide

When gamma-methyl-1H-imidazole-1-propanamine is treated with 5-chlorothiophene-2-carbonyl chloride by the procedure of Example 36, the above compound, m.p. 141°–143° C., is obtained.

EXAMPLE 40

5-Chloro-N-[4-(1H-imidazol-1-yl)-2-butenyl]-2-thiophene carboxamide

A mixture of 100 g. of 1.4-dichlorobutene, 74 g. of potassium phthalimide and 1500 ml. of dimethylformamide was stirred at room temperature for 24 hours. The reaction mixture was concentrated to remove the solvent and residue taken up with 2000 ml. of boiling hexane and again concentrated. The residue was dissolved in methylene chloride, washed with water, dried over magnesium sulfate and concentrated to obtain 46 g. of N-(4-chloro-2-butenyl)isoindole-1,3(2H)-dione, m.p. 79°–81° C.

A mixture of 23.5 g. of N-(4-chloro-2-butenyl)-isoindole-1,3(2H)-dione, 11.0 g. of sodium imidazole and 200 ml. of dimethyl formamide was heated on the steam bath for 18 hours and concentrated to remove the solvent; the residue was taken up in methylene chloride, washed with water, dried with magnesium sulfate and again concentrated. The residue was dissolved in hot ethylacetate and allowed to cool and N-[4-(1H-imidazol-1-yl)-2-butenyl]isoindole-1,3-(2H)-dione, m.p. 106°–108° C., was obtained.

A mixture of 26.8 g. of N-[4-(1H-imidazol-1-yl)-2-butenyl]isoindole-1,3-(2H)-dione, 4.85 ml of hydrazine hydrate and 250 ml. of ethanol was heated at reflux temperature for 6 hours. The mixture was cooled and 225 ml. of 3N hydrochloric acid was added and the mixture was again heated at reflux temperature for 3 hours. The precipitate was filtered off and the mother liquor was concentrated once more and then treated with saturated potassium carbonate solution. Extraction with methylene chloride resulted in 4-(1H-imidizol-1-yl)-2-butenamine, obtained as an oil.

A solution of 1.65 g. of 4-(1H-imidazol-1-yl)-2-butenamine, 60 ml. of methylene chloride and 12 ml. of 1N sodium hydroxide was stirred and 1.8 g. of 5-chlorothiophen-2-carbonyl chloride was added. The reaction mixture was stirred for 18 hours, 40 ml. of methylene chloride and 5 ml. of 1N sodium hydroxide was added and the layers were separated. The organic layer was washed with water, dried over magnesium sulfate and concentrated and the desire compound was obtained, m.p. 115°–117° C.

We claim:

1. A compound selected from the group consisting of those of the formula:

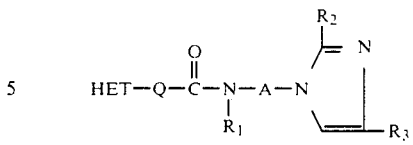

wherein A is a divalent moiety of the formulae:

$$-C_nH_{2n}- \text{ or } -CH_2CH=CHCH_2-$$

wherein n is an integer from 2 to 8, inclusive; $R_1$ is hydrogen, alkyl ($C_1$–$C_3$) or benzyl; $R_2$ and $R_3$ are each hydrogen, alkyl($C_1$–$C_3$) or phenyl, Q is a divalent moiety of the formulae:

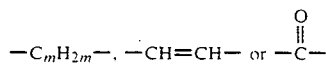

wherein m is zero, 1, 2 or 3; and HET is a heterocyclic moiety of the formulae:

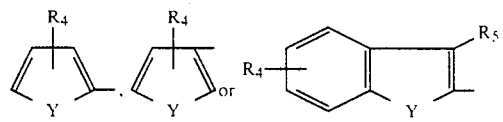

wherein Y is oxo or thio; $R_4$ is hydrogen, halogen, dihalogen, lower alkyl or nitro; and $R_5$ is hydrogen or halogen; and the pharmacologically acceptable acid-addition salts thereof.

2. The compound according to claim 1; N-[3-(1H-imidazol-1-yl)propyl]-2-furanecarboxamide.

3. The compound according to claim 1; 5-chloro-N-[4-(1H-imidazol-1-yl)butyl]-2-thiophenecarboxamide.

4. The compound according to claim 1; N-[3-(1H-imidazol-1yl)propyl]-5-nitro-2-furanecarboxamide.

5. The compound according to claim 1; N-[3-(1H-imidazol-1-yl)propyl]-α-oxo-thiophene acetamide.

6. The compound according to claim 1; 3-chloro-N-[2-(1H-imidazol-1-yl)ethyl]-2-benzo[b]thiophenecarboxamide.

7. The compound according to claim 1; N-[4-(1H-imidazol-1-yl)butyl]-2-thiophenecarboxamide.

8. The compound according to claim 1; 5-chloro-N-[3-(1H-imidazol-1-yl)propyl]-2-thiophenecarboxamide.

9. The compound according to claim 1; 3-chloro-N-[3-(1H-imidazol-1-yl)propyl]-2-benzo[b]thiophenecarboxamide.

10. The compound according to claim 1; 4,5-dibromo-N-[3-(1H-imidazol-1-yl)propyl]-2-thiophenecarboxamide.

11. The compound according to claim 1; 5-chloro-N-[3-(1H-imidazol-1-yl)propyl]-2-benzo[b]thiophenecarboxamide.

12. The method of inhibiting thromboxane synthetase enzyme in a mammal which comprises administering internally to said mammal an effective thromboxane synthetase enzyme inhibiting amount of a compound of claim 1.

13. A thromboxane synthetase enzyme inhibiting composition of matter in dosage unit form comprising from about 10 mg. to about 700 mg. of a compound of claim 1 in association with a pharmaceutical carrier.

* * * * *